United States Patent
Gottschalk-Gaudig et al.

(10) Patent No.: US 9,527,874 B2
(45) Date of Patent: Dec. 27, 2016

(54) PROCESS FOR SURFACE MODIFICATION OF PARTICULATE SOLIDS

(71) Applicant: Wacker Chemie AG, Munich (DE)

(72) Inventors: Torsten Gottschalk-Gaudig, Mehring (DE); Carl-Heinz Ehrke, Zabeltitz (DE); Helmut Maginot, Burgkirchen (DE)

(73) Assignee: Wacker Chemie AG, Munich (DE)

( * ) Notice: Subject to any disclaimer, the term of this patent is extended or adjusted under 35 U.S.C. 154(b) by 8 days.

(21) Appl. No.: 14/381,107

(22) PCT Filed: Mar. 5, 2013

(86) PCT No.: PCT/EP2013/054320
§ 371 (c)(1),
(2) Date: Aug. 26, 2014

(87) PCT Pub. No.: WO2013/135521
PCT Pub. Date: Sep. 19, 2013

(65) Prior Publication Data
US 2015/0025261 A1    Jan. 22, 2015

(30) Foreign Application Priority Data
Mar. 12, 2012   (DE) .......... 10 2012 203 826

(51) Int. Cl.
| | | |
|---|---|---|
| *C01B 33/159* | (2006.01) | |
| *C07F 7/18* | (2006.01) | |
| *C09C 3/12* | (2006.01) | |
| *C09C 1/30* | (2006.01) | |
| *C07F 7/12* | (2006.01) | |

(52) U.S. Cl.
CPC .............. *C07F 7/188* (2013.01); *C07F 7/126* (2013.01); *C09C 1/3081* (2013.01); *C09C 3/12* (2013.01); *C01P 2002/02* (2013.01); *C01P 2002/70* (2013.01); *C01P 2002/89* (2013.01); *C01P 2004/62* (2013.01); *C01P 2006/12* (2013.01)

(58) Field of Classification Search
USPC ........................................ 423/335, 610, 625
See application file for complete search history.

(56) References Cited

U.S. PATENT DOCUMENTS

| | | |
|---|---|---|
| 5,686,054 A | 11/1997 | Heinemann |
| 6,696,034 B2 | 2/2004 | Nozawa et al. |
| 7,276,615 B2 | 10/2007 | Gottschalk-Gaudig et al. |
| 2003/0100631 A1 | 5/2003 | Heinemann |
| 2003/0138715 A1* | 7/2003 | Barthel et al. ............. 430/108.3 |

FOREIGN PATENT DOCUMENTS

| | | |
|---|---|---|
| DE | 4419234 | 12/1995 |
| DE | 10150274 | 4/2003 |
| EP | 0686676 A1 | 12/1995 |
| EP | 1184425 A1 | 3/2002 |
| EP | 1302444 A1 | 4/2003 |
| GB | 887257 A | 1/1962 |
| JP | 2002-69330 A | 3/2002 |
| JP | 2004-339508 A | 12/2004 |
| WO | 2007/084245 A | 7/2007 |

* cited by examiner

*Primary Examiner* — Pancham Bakshi
(74) *Attorney, Agent, or Firm* — Brooks Kushman P.C.

(57) ABSTRACT

Improved utilization of organosilicon compounds in hydrophobicizing finely divided particulate solids is accomplished by metering a partial amount of unreacted solids with organosilicon containing offgases derived from admixing and reacting a major portion of solids with organosilicon compounds and admixing the offgas-treated solids with the major portion of solids to be treated.

11 Claims, No Drawings

PROCESS FOR SURFACE MODIFICATION OF PARTICULATE SOLIDS

CROSS-REFERENCE TO RELATED APPLICATIONS

This application is the U.S. National Phase of PCT Appln. No. PCT/EP2013/054320 filed Mar. 5, 2013, which claims priority to German Application No. 10 2012 203 826.4 filed Mar. 12, 2012, the disclosures of which are incorporated in their entirety by reference herein.

BACKGROUND OF THE INVENTION

1. Field of the Invention

The invention relates to a process for modifying finely divided particulate solids by gas phase silylation.

2. Description of the Related Art

Surface modified finely divided particulate solids such as silicas and specifically pyrogenic silicas are used inter alia for controlling the flow properties of adhesive, sealant and coating materials, for improving the mechanical properties of elastomers, and for controlling the charge and flow properties of powders such as toners or powder finishes.

The surface modification of the finely divided particulate solids is preferably a chemical, irreversible modification in that the modifying agent is attached to the particle surface via a chemical bond. Typical modifying agents to enter a chemical reaction with the particle surface are organosilanes or organosiloxanes. These bind with the filler surface to form stable solid-silicon-oxygen bonds.

Processes for surface modification of finely divided particulate solids with organosilanes or organosiloxanes are known, for example from DE 10150274 or EP 0686676.

The common feature of the processes described therein is a first step of intensively mixing the unmodified finely divided particulate solids with the organosilane and the organosiloxane, respectively, these being added to the solid either as a vapor or as a very finely divided aerosol. The solid and the organosilane/organosiloxane are then made to react thermally, followed by a purifying operation in which any adherent elimination products or excess modifying reagents are removed from the particle surface. Preferably, the offgases generated in the individual processing steps are at least partly recycled into the mixer in order to limit losses of organosilane/organosiloxane. It transpired, however, that there are technical reasons why complete recycling of the offgases is not possible and at least a portion of the offgases has to be flued from the plant in order to prevent the accumulation of elimination products and supply fresh $N_2$ for inertization.

The offgas to be flued first has to be freed of entrained solids. This is accomplished using known methods of separating solids from gas streams such as, for example, filters with or without cyclones.

The organosilanes/organosiloxanes in the offgas stream are withdrawn from the reaction and thus lead to a significant reduction in the yield of product based on the amount of organosilane/organosiloxane used. The organosilicon compounds in the offgas stream further lead to fouling and hence blinding of the filter fabric, so pressurization occurs upstream of filters and the system has to be shut down to change the filter. This leads to a significant increase in costs through the increased consumption of filter materials and manufacturing outage. Reducing the plant throughput does extend the filter on-stream time, but only at the expense of the manufacturing output. The problem of filter fabric blinding due to fouling is aggravated when using sparingly volatile organosilicon compounds such as, for example, organosiloxanes that are not vaporizable without decomposition and thus are in the state of a finely divided aerosol when they become mixed with the finely divided particulate solids.

EP 1184425 A describes a process for surface modification of silicas with organohalosilanes which comprises a step of both mixing and reacting the silica with vaporous, i.e. volatile, organohalosilane in a fluidization vessel. A substream of the silica to be modified is metered into the offgas line of the fluidization vessel, then separated from the offgas and finally returned into the fluidization vessel for reaction, while the temperature in the fluidization vessel is in the range from 400 to 600° C. This process is disadvantageous because the sub-stream of the silica separated from the offgas is metered directly into the hot nitrogen-fluidized reaction zone and thereby gives rise to inhomogeneously modified products, i.e., products having a widely varying degree of silylation. The process described also involves a complex, difficult-to-control operation featuring additional vessels and valves to return the sub-stream into the reaction after it has been separated.

SUMMARY OF THE INVENTION

The invention provides a process for producing surface modified particulate finely divided solid F of large surface area, which process comprises
a process step (A) of mixing a partial amount of unmodified finely divided solid F1 with organosilicon compound to produce an offgas comprising organosilicon compound,
a process step (B) of reacting the mixture of unmodified finely divided solid F1 with organosilicon compound to produce surface modified finely divided solid F with or without an offgas comprising organosilicon compound,
a process step (C) of freeing the surface modified finely divided solid F of adsorbed byproducts and unconverted organosilicon compound which are obtained as offgas,
a process step (D) of metering a further partial amount of unmodified finely divided solid F1 into the offgas obtained in process steps (A), (C) and, if applicable, (B) to mix the solid F1 with organosilicon compound in the offgas,
and a process step (E) of the mixture obtained in process step (D) being fed in process step (A) to the partial amount of unmodified finely divided solid F1 and organosilicon compound.

It was found, then, that, surprisingly, the surface modification of particulate finely divided solid F1 of large surface area with organosilicon compounds, in particular of sparingly volatile organosilicon compounds, which are preferably mixed as a finely divided aerosol with the finely divided particulate solids F1, by metering of unmodified finely divided particulate solid F1 into the offgas stream upstream of filters and returning the solid particles into the mixer which have become laden with organosilicon compound in the gas stream, leads to a distinct improvement in the on-stream time of the filters and also reduces the losses of organosilicon compound without adversely affecting the quality of the products.

The reaction in process step (B) is a silylation of solid F1 by the organosilicon compounds, which are one compound or any desired mixtures of organosilicon compounds.

Preferred organosilicon compounds are organosilanes of general formula (I)

$$X_{1+x}\text{—}SiR^4{}_{2-x}\text{—}(CH_2)_y\text{—}Y \qquad (I),$$

where
X represents halogen, nitrogen, OR³ or OCOR³,
R³ represents C—O bonded $C_1$-$C_{15}$ hydrocarbyl, preferably $C_1$-$C_8$ hydrocarbyl, more preferably $C_1$-$C_3$ hydrocarbyl, or acetyl,
R⁴ represents a hydrogen atom or optionally NC—, OCN—, 2R²N—, HOOC—, R²OOC—, halogen-, acryloyl-, epoxy-, HS—, HO— or 2R²NOC-substituted Si—C bonded $C_1$-$C_{20}$ hydrocarbyl, preferably $C_1$-$C_8$ hydrocarbyl, more preferably $C_1$-$C_3$ hydrocarbyl, or aryl, or $C_1$-$C_{15}$ hydrocarbyloxy, preferably $C_1$-$C_8$ hydrocarbyloxy, more preferably $C_1$-$C_4$ hydrocarbyloxy, in each of which one or more mutually nonadjacent methylene units may be replaced by —O—, —CO—, —COO—, —OCO—, or —OCOO—, —S—, or —NR²— groups and in which one or more mutually nonadjacent methine units may be replaced by —N═ or —P═ groups,
Y represents hydrogen, unsaturated or mono- or polyunsaturated $C_1$-$C_{20}$ hydrocarbyl, —OC(O)C(R)═CH₂, -vinyl, -hydroxyl, -halogen, phosphonato, —NCO, —NH—C(O)—OR¹, -glycidoxy, —SH, acid anhydrides, such as succinic anhydride,
R, R¹ each represent $C_1$-$C_{15}$ hydrocarbyl, preferably $C_1$-$C_8$ hydrocarbyl, more preferably $C_1$-$C_3$ hydrocarbyl)
v represents integral values from 0 to 10, preferably 0-5 and more preferably 0, 1 or 3, and
x' represents 1 or 2.

Preferred organosilicon compounds also include organosiloxanes constructed of A units of general formula (IIa) and B units of formulae (IIb-d)

$(R^5_3SiO_{1/2})$           (IIa), $(R^5_2SiO_{2/2})$           (IIb), $(R^5SiO_{3/2})$           (IIc), $(SiO_{4/2})$           (IId), where the organosiloxanes may contain 1 or 2 —X groups attached to silicon atoms, where X is as defined above, and the organosiloxanes may contain the ═SiX or ═SiX2 groups in a number C and A, B and C are subject to the following condition:
1≤B≤5000, preferably 3≤B≤1000, more preferably 5≤B≤100 and in one specific mode 5≤B≤50, with the proviso that B≥A+C, preferably B≥A+C and more preferably B≥2×(A+C), where A+C=0 is subject to the condition 10≤B≤100, preferably A+C≤20 and more preferably A+C≤2, while the ratio of A to C is freely choosable, and R5 represents an optionally mono- or polyunsaturated, monovalent, optionally halogenated Si—C bonded hydrocarbyl of 1 to 18 carbon atoms, preferably 1 to 8 carbon atoms and more preferably 1 to 3 carbon atoms.

Organosilanes of general formula I which are preferably used are organosilanes where Y represents hydrogen, vinyl, acrylate, methacrylate, glycidoxy, —SH, —OH, primary amino —NH₂, secondary amino radicals —NHR such as N-monomethyl, N-monoethyl, N-monopropyl, N-monobutyl, N-cyclohexyl or anilino, tertiary amino radicals —NR₂ such as N,N-dimethyl, N,N-diethyl, N,N-dipropyl, N,N-dibutyl, N,N-methylethyl, N,N-methylpropyl, N,N-ethylpropyl or N,N-methylphenyl or morpholino, pyrrolyl, indolyl, pyrazoyl, imidazoyl or piperidyl, quaternary amino radicals such as the N,N,N-trimethylammonium, N,N,N-triethylammonium or N,N,N-tripropylammonium radical, where Y represents phosphonato, —P(O)(OR)₂ (R═methyl, ethyl, phenyl), isocyanato and protected isocyanato-N(H)C(O)G, where the protective group G detaches as H-G (H-G=methyl 2-hydroxybenzoate, 2-hydroxypyridine, 1-hydroxymethyl-1,2,4-triazole, N,N-diethylhydroxylamine, 2-butanone oxime, dimethyl malonate, ethyl acetoacetate, diisopropylamine, benzyltert-butylamine, tert-butylmethylamine, tert-butylisopropylamine, 2-isopropyl-imidazole, 3,5-dimethylpyrazole and ε-caprolactam) on thermal exposure, or where Y represents dihydro-3-yl-2,5-furandione.

Examples of R⁴ include alkyl radicals such as methyl, ethyl, propyl radicals such as isopropyl or n-propyl, butyl radicals such as t- or n-butyl, pentyl radicals such as neopentyl, i-pentyl or n-pentyl, hexyl radicals such as n-hexyl, n-heptyl, octyl radicals such as 2-ethylhexyl or n-octyl, decyl radicals such as n-decyl, dodecyl radicals such as n-dodecyl, hexadecyl radicals such as n-hexadecyl, octadecyl radicals such as n-octadecyl, aryl radicals such as phenyl, biphenyl or naphthenyl, alkylaryl radicals such as benzyl, ethylphenyl, toluoyl or xylyl. Preference is given to methyl, ethyl or propyl radicals such as isopropyl or n-propyl and more preferably methyl.

Preference is given to using organosiloxanes of general formula II.

Examples of organosiloxanes include linear or cyclic dialkylsiloxanes having on average more than 2, preferably more than 10 and preferably less than 100, more preferably less than 50 dialkylsiloxy units.

Dialkylsiloxanes are preferably dimethylsiloxanes, more preferably polydimethylsiloxanes.

Examples of linear polydimethylsiloxanes include linear polydimethylsiloxanes having the end groups: trimethylsiloxy, dimethylhydroxysiloxy, dimethylchlorosiloxy, methyldichlorosiloxy, dimethylmethoxysiloxy, methyldimethoxysiloxy, dimethylethoxysiloxy, methyldiethoxysiloxy, dimethylacetoxysiloxy, methyldiacetoxysiloxy; while trimethylsiloxy and dimethylhydroxysiloxy are particularly preferred.

End groups may be the same or different.

Abovementioned organosilanes or organosiloxanes can be used for the silylation in pure form or in any desired mixtures, the silylation with organosiloxanes is preferred.

The reacting in process step (B), viz., the surface treatment, is preferably conducted in an atmosphere that does not lead to oxidation of the surface modified finely divided r solid F, i.e., preferably in an atmosphere containing less than 10% by volume of oxygen, more preferably less than 2.5% by volume, best results being achieved at less than 1% by volume of oxygen.

Process step (B) produces not only the surface modified finely divided solid F but also an offgas comprising unconverted organosilicon compound and byproducts.

The process, in particular process steps (A), (B) and (C), may be conducted as a batch operation or as a continuous operation. A continuous mode of reaction management is preferable for technical reasons.

Process steps (A), (B) and (C) are each preferably carried out in a separate vessel, i.e., under spatial separation. Possible means to achieve spatial separation include, for example, flaps, locks, pumps or other apparatus.

Temperatures for conducting process step (A), i.e., mixing unmodified finely divided solid F1 with organosilicon compound, are preferably in the range from −30 to 250° C., preferably in the range from 0 to 200° C. and more preferably in the range from 20 to 150° C.; one specific mode involves conducting the coating step at 30 to 120° C.

The residence time in process step (A) is 1 min-24 h, preferably 15 min to 300 min and more preferably, for space-time yield reasons, 15 min to 240 min.

The pressure in process step (A) ranges from slight underpressure of down to 0.2 bar up to an overpressure of 100 bar, while there are technical reasons to prefer standard pressure, i.e., unpressurized operation relative to external/atmospheric pressure.

The organosilicon compounds are preferably added in liquid form or vapor form, more particularly admixed to the unmodified finely divided solid F1.

It is particularly preferable to admix the organosilicon compounds in liquid form, i.e., as a finely divided aerosol. The aerosol preferably has a settling velocity of 0.1-20 cm/s. Settling velocity may be measured using, for example, laser Doppler anemometry and/or phase Doppler anemometry.

The organosilicon compounds may be admixed in pure form or as solutions in known industrially used solvents, for example, alcohols such as methanol, ethanol, or i-propanol, ethers such as diethyl ether, THF, or dioxane, or hydrocarbons such as hexanes or toluene. Their concentration in the solution is 5-95 wt %, preferably 30-95 wt %, more preferably 50-95 wt %.

Admixture in pure form is particularly preferred.

Admixing is preferably accomplished using nozzle technologies, or comparable technologies, such as effective jetting techniques, such as jetting in 1-fluid nozzles under pressure, preferably 5 to 20 bar, spraying in 2-fluid nozzles under pressure, preferably gas and liquid 2-20 bar, atomizing with atomizers or gas-solid exchange assemblies with movable, rotating or static internals to achieve homogeneous distribution of the organosilicon compounds.

Solid F1 is preferably in a fluidized state in process step (A). The direction of injection of the aerosol of the organosilicon compounds is preferably into the fluidized solid F1 and more preferably downward onto the fluidized solid F1.

Preferably, the mixing with the organosilicon compounds in process step (A) and the reacting in process step (B) are effected under mechanical or gasborne fluidization. Mechanical fluidization is particularly preferred.

Gasborne fluidization may be effected using any inert gases that do not react with the organosilicon compounds, the finely divided solid F1, and the modified solid F, i.e., do not lead to concurrent reactions, degradation reactions, oxidative events or flame or explosive phenomena, such as preferably $N_2$, Ar, other noble gases, $CO_2$, etc. Superficial velocities for feeding the fluidizing gases are preferably in the range from 0.05 to 5 cm/s and more preferably in the range from 0.5 to 2.5 cm/s.

That form of mechanical fluidization is particularly preferred which is carried out without gas requirements in addition to and beyond those needed for inertization, by means of blade stirrers, anchor stirrers, or other suitable stirring elements.

Preferably from 1 to 50 parts by weight, more preferably from 2 to 30 parts by weight and especially from 5 to 20 parts by weight, of solid F1 are metered into the offgas in process step (D) per 100 parts by weight of solid F1 used in process step (A).

Product temperatures for the reaction in process step (B) are preferably 20-400° C., preferably 50-380° C. and more preferably in the range from 60 to 350° C.

In a preferred embodiment, the reaction is carried out at a constant wall temperature. This means that the wall temperature of the reaction vessel is in a range of 20-400° C., preferably in a range of 50-380° C. and more preferably in a range of 60-350° C.

In a further preferred embodiment, the reaction in process step (B) takes place in a temperature gradient in the range from 20° C. to 400° C., preferably in a range of 50 to 380° C. and more preferably in a range of 60 to 350° C. in that the reaction temperature rises in the course of the reaction time.

This means that the wall temperature of the reaction vessel is in a range of 20-300° C., preferably in a range of 50-250° C. and more preferably in a range of 60-200 at the start of the reaction and in a range of 30-400° C., preferably in a range of 60-380° C. and more preferably in a range of 70 to 350° C. at the end of the reaction subject to the proviso that the temperature difference between the wall temperature at the start of the reaction and the wall temperature at the end of the reaction is in a range of 10 to 200° C., preferably 20 to 180° C. and more preferably 30 to 150° C. and the wall temperature is lower at the start of the reaction than at the end of the reaction.

This further means that the product temperature is in a range of 20-300° C., preferably in a range of 50-250° C. and more preferably in a range of 60-200 at the start of the reaction and in a range of 30-400° C., preferably in a range of 60-380° C. and more preferably in a range of 70 to 350° C. at the end of the reaction subject to the proviso that the temperature difference between the product temperature at the start of the reaction and the product temperature at the end of the reaction is in a range of 10 to 200° C., preferably 20 to 180° C. and more preferably 30 to 150° C. and the product temperature is lower at the start of the reaction than at the end of the reaction.

This means that the form of process implementation, i.e., whether the process is implemented as a continuous operation or as a batch operation, determines whether the temperature gradient is dependent on position dT/dx (as is the case with a continuous operation) or on time dT/dt (as is the case with a batch operation).

The reaction temperature in process step (B), i.e., the wall/product temperature, or the gradient thereof can be attained as follows:

1. Continuous Operation (i.e., dT/Dx):
   The solid F1 is carried by gasborne or mechanical fluidization/transportation through a heating zone of increasing wall temperature. The increase in the wall temperature can be continuous or stepwise. In the case of a stepwise increase, the reaction zone may consist of up to 10 separate heating zones of differing temperature, preferably 5 separate heating zones of differing temperature, more preferably 3 separate heating zones of differing temperature and specifically 2 separate heating zones which differ in temperature. Optionally, flaps may separate the individual heating zones from each other. The attitude of the reaction vessel may be vertical or horizontal. A vertical attitude is preferred. A vertical attitude makes it possible for the solid F1 to travel through the reaction zone upwardly or downwardly. Downwardly is preferred.

or:

The solid F1 is carried by gasborne or mechanical fluidization/transportation through separate reaction vessels of differing, i.e., increasing, wall temperature. The reaction cascade may consist of up to 10 reaction vessels of differing wall temperature, preferably up to 5 reaction vessels of differing wall temperature, more preferably up to 3 reaction vessels of differing wall temperature and specifically 2 reaction vessels which differ in wall temperature. The attitude of the reaction vessels may be vertical or horizontal. A vertical attitude is preferred. A vertical attitude makes it possible for the solid F1 to travel through the reaction zone upwardly or downwardly. Downwardly is preferred.

or:

The solid F1 is carried by mechanical fluidization/transportation through an upright reaction vessel. The reaction vessel is heated in its lower part to the maximum reaction temperature. A temperature difference accordingly becomes established in the reaction vessel between the upper part of the reaction vessel (where the temperature is lowest) and the lower part of the reaction vessel (where the temperature is highest). This temperature difference may be controlled by suitable stirring technology for example.

2. Batch Operation

The solid F1 is fluidized in the reaction vessel using an inert gas or mechanical stirring. The reaction temperature in the reaction vessel is increased gradually, i.e., in the form of a ramp or stepwise, in the course of the reaction.

The residence time per reaction temperature is preferably between 5 min and 240 min, more preferably between 10 min and 180 min and especially between 15 min and 120 min.

The reaction zone may for example be heated via the vessel wall, for example by electric heating or using heat transfer fluid or steam. Heating coils for example may be optionally employed in the reaction vessel.

Heating may optionally be applied from the outside via infrared radiators.

Wall and product temperatures may be measured by means of customarily employed measuring instruments such as thermocouples, resistance thermometers, bimetallic thermometers, IR sensors or others.

Total reaction time ranges from 10 min to 48 h, preferably from 15 min to 5 h and more preferably from 15 min to 4 h.

Process step (A) may optionally include the addition of protic solvents, such as liquid or vaporizable alcohols or water; isopropanol, ethanol and methanol are typical alcohols. Mixtures of the abovementioned protic solvents can also be added. The amount of protic solvent added is preferably in the range from 1 to 50 wt % and more preferably in the range from 5 to 25%, all based on the solid F. Water is particularly preferred.

When catalysts are used, there is a choice between adding acidic catalysts, acidic in the sense of a Lewis acid or a Brönsted acid, such as hydrogen chloride, or adding basic catalysts, basic in the sense of a Lewis base or a Brönsted base, such as ammonia or amines such as triethylamine. These are preferably added in traces, i.e., at less than 1000 ppm. It is particularly preferable not to add any catalysts.

The temperature at which the surface modified solid F is purified of offgas in process step (C) is preferably a purification temperature of 20 to 200° C., preferably 50° C. to 180° C., more preferably in the range from 50 to 150° C.

Said purification step (C) is preferably characterized by agitation, more preferably by slow agitation and minimal commixing. Stirring-element adjustment and movement is advantageously such as to preferably produce some mixing and some fluidization but not full fluidization.

Purification step (C) may further be characterized by enhanced gas input, preferably corresponding to a superficial gas velocity of 0.001 to 10 cm/s, more preferably 0.01 to 1 cm/s. This can be accomplished using any inert gases that do not react with the organosilicon compounds, the solid F1, and the modified solid F, i.e., do not lead to concurrent reactions, degradation reactions, oxidative events or flame or explosive phenomena, such as preferably $N_2$, Ar, other noble gases, $CO_2$, etc.

In a particularly preferred embodiment, unconverted organosilicon compounds recovered from the offgas are returned from purification step (C) back into process step (A); this recycling can be partial or complete, preferably at 10-90% of the entire stream of gas volumes exiting from purification step (C). The offgas from purification step (C) is preferably returned back into process step (A). This is preferably accomplished in suitably temperature-regulated equipment.

This recycling preferably takes place in uncondensed phase, i.e., as gas or as vapor. This recycling may take the form of mass transport along a pressure equalizer or as a controlled form of mass transport by applying the industrially customary systems for gas transportation, such as fans, pumps, compressed air diaphragm pumps. Since it is preferable to recycle the uncondensed phase, it may be advisable to heat the return lines.

The return rate for the offgases may be between preferably 5 and 100 wt %, based on the overall mass, more preferably between 30 and 80 wt %. The return rate based on 100 parts of freshly used organosilicon compounds may be between 1 and 200 parts, preferably from 10 to 30 parts.

The organosilicon compounds or the offgases are preferably returned into process step (A) in a continuous manner.

Processes for mechanically compacting the solid F may additionally be utilized during process step (A) or following process step (C), for example press rolling, grinding assemblies, such as edge mills and such as ball mills, continuous or batchwise, compaction by screws or screw mixers, screw compactors, briquetters, or compaction by aspiring the air or gas content by suitable vacuuming methods.

Particular preference is given to mechanical compaction during the modifying reaction in step (B) by press rolling, the abovementioned grinding assemblies such as ball mills or compaction by screws, screw mixers, screw compactors, briquetters.

In a further particularly preferred procedure, process step (C) is followed by the utilization of processes for mechanically compacting the solid F, such as compaction by aspirating the air or gas content by suitable vacuuming methods or press rolling or combination thereof.

In addition, in a particularly preferred procedure, process step (C) may be followed by employment of processes for deagglomerating the solid F, such as pin mills, hammer mills, countercurrent mills, impact mills or devices for millbase sifting.

To ensure an inert gas atmosphere, i.e., a gas atmosphere of preferably less than 10% by volume of oxygen, more preferably less than 2.5% by volume and in a specific mode less than 1% by volume of oxygen, during process steps (A), (B), (C) and (D), a feed of fresh nitrogen is preferably provided to the plant. This may be accomplished via specific feedpoints such as gas stubs on the individual apparatuses, such as mixers, reactors, dryers, and/or in the form of storage purge gas or as transportation gas in the gasborne transportation of the unmodified finely divided particulate solids F1 into the plant and/or of the modified finely divided particulate solids F within the plant.

The volume fraction of the fresh nitrogen feed per 1 hour as a proportion of the overall volume of the plant is in the range from 1 to 1000%, preferably in the range from 50 to 800% and more preferably in the range from 100 to 500%.

To avoid an overpressure in the plant, therefore, the use of an inert gas atmosphere entails that at least some of the offgas from process steps (A), (B) and (C) has to be flued out of the plant.

This is accomplished by the offgases from process steps (A), (B) and (C) being merged into one offgas line, fed to a solids collector and subsequently the offgas which has been freed of solids being properly disposed of. The solids collectors may be, for example, cyclones, filters or any desired combinations thereof. The offgas line preferably has metered into it countercurrently at a point upstream of the first solids collector a sub-stream of the unmodified finely divided particulate solid F1. The unmodified solid F1 becomes laden with the organosilicon compounds in the offgas, or the silicon-containing elimination, condensation or addition-polymeration products resulting therefrom, and the solid F thus laden is introduced into the mixer in process step (A).

Preferably, the sub-stream of the unmodified finely divided particulate solid F1 is branched off at a point downstream of the solids metering into the mixer and metered into the offgas line. The solids metering can be effected volumetrically and/or gravimetrically using known methods. Gravimetric metering is preferred.

Metering the particle sub-stream into the offgas line can be effected using customary transportation techniques. Preference is given to transportation via solids pumps such as, for example, compressed air diaphragm pumps.

The temperature of the offgas here is preferably at least 10° C., more preferably at least 50° C. above the highest dewpoint temperature of those individual components in the offgas which are vaporizable without decomposing.

The temperature of the offgases is in the range from 50° C. to 400° C., preferably in the range from 100° C. to 300° C. and more preferably in the range from 150 to 250° C.

The offgas is preferably cooled, for example by heat exchanger or admixture of chill gas, preferably chill nitrogen.

In the process of the present invention, the loss of organosilicon compound used is preferably less than 50%, more preferably less than 40%, especially less than 30% and in one advantageous mode less than 20%.

The process of the present invention preferably utilizes a finely divided particulate solid F1 having a mean particle size below 100 µm, and more preferably having a mean primary particle size in the range from 5 to 100 nm. These primary particles cannot exist in isolation, but are constituent parts of larger aggregates and agglomerates.

Preferred solids F1 are metal oxides, silicates, aluminates, titanates, or aluminum sheet-silicates, such as bentonites, such as montmorillonites, or smectites or hectorites.

Metal oxides are preferred solids. The metal oxide preferably has a specific surface area of preferably 0.1 to 1000 m²/g (measured by the BET method to DIN 66131 and 66132), more preferably of 10 to 500 m²/g and most preferably of 30 to 450 m²/g. The aforementioned definitions are also to be understood in the context of the present invention as providing the preferred definition of a large specific surface area.

The metal oxide may preferably comprise aggregates (as defined in DIN 53206) in the 100 to 1000 nm range of diameters, in which case the metal oxide comprises agglomerates (as defined in DIN 53206) which are constructed of aggregates and which is able to have sizes of 1 to 1000 µm depending on the external shearing stress (caused by the measuring conditions, for example).

For reasons of industrial handleability, the metal oxide is preferably an oxide having a covalent component in the metal-oxygen bond, preferably an oxide of the main and transition group elements, as of the 3rd main group, such as boron oxide, aluminum oxide, gallium oxide or indium oxide, or of the 4th main group such as silicon dioxide, germanium dioxide, or tin oxide or dioxide, lead oxide or dioxide, or an oxide of the 4th transition group, such as titanium dioxide, zirconium oxide, or hafnium oxide. Other examples of suitable metal oxides are stable oxides of nickel, of cobalt, of iron, of manganese, of chromium or of vanadium.

Particular preference for use as metal oxide is given to aluminum(III) oxide, titanium(IV) oxide and silicon(IV) oxide, for example wet-chemically produced, for example precipitated, silicas or silica gels, aluminum oxides, titanium dioxides or silicon dioxides as produced in processes at elevated temperature, examples being pyrogenically produced aluminum oxides, titanium dioxides or silicon dioxides or silica.

Particular preference for use as metal oxide is given to pyrogenic silica as produced in a flame reaction, preferably from organosilicon compounds, for example from silicon tetrachloride, methyl dichlorosilane, hydrogentrichlorosilane or hydrogenmethyldichlorosilane, or other methylchlorosilanes or alkylchlorosilanes, including admixtures with hydrocarbons, or any desired volatilizable or sprayable mixtures of organosilicon compounds as mentioned, or hydrocarbons, for example in a hydrogen-oxygen flame, or else in a carbon monoxide-oxygen flame. The silica may electively be produced with or without further addition of water, for example in the purification step; preference is given to no addition of water.

The pyrogenic silica preferably has a fractal surface dimension of preferably not more than 2.3, more preferably not more than 2.1 and yet more preferably of 1.95 to 2.05, the fractal surface dimension $D_s$ being defined as:
particle surface area A is proportional to particle radius R to the power of $D_s$.

The fractal surface dimension was determined using small angle x-ray scattering (SAXS).

The silica preferably has a fractal mass dimension Dm of preferably not more than 2.8, more preferably equal to or below 2.7 and more preferably of 2.4 to 2.6. Fractal mass dimension Dm is defined as:
particle mass M is proportional to particle radius R to the power of Dm.

The fractal mass dimension was determined using small angle x-ray scattering (SAXS).

The modified particulate solids F preferably have a carbon content, as determined via elemental analysis, of preferably 0.1 to 20 wt %, more preferably 0.5 to 15 wt % and yet more preferably in the range from 1 to 12 wt %.

Surface silanol groups SiOH are present in the solids F at from 0.1 to 1.7 SiOH/nm², preferably 0.1 to 1.5 SiOH/nm², more preferably 0.1 to 1.0 SiOH/nm² and in one specific mode 0.1 to 0.75 SiOH/nm². Surface silanol group density here is determined using acid-base titration.

The solids F are further characterized by a particularly homogeneous modification of the surface. This means that the water wettable fraction of modified particulate solids F is less than 10 wt %, preferably less than 5 wt %, more preferably less than 1 wt %, yet more preferably less than 0.1 wt %, and in one specific mode, undetectable. The water wettable fraction is determined by shaking a defined amount of powder in water.

The examples which follow serve to further elucidate the invention.

EXAMPLE 1

The experiment is carried out in a continuous process plant consisting of a mixer, an upright reactor and a dryer, while the offgases of mixer, reactor and dryer are collected and flued off out of the plant via a filter. An aliquot of the hydrophilic pyrogenic silica is metered into the offgas stream at a point upstream of the filter and returned into the mixer after cleaning off the filter. Filter loading is determined by determining the pressure drop at the filter.

Into the continuous plant are added in the mixer at a temperature of 30° C. under inert gas $N_2$, under mechanical fluidization by stirrer, to a mass flow of 900 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D), 180 g/h of a dimethylhydroxysiloxy-terminal polydimethylsiloxane having a viscosity at 25° C. of 20 mPas in liquid, very finely divided form by jetting through a one-fluid nozzle as an aerosol (pressure 10 bar). In addition, a further 100 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D) are metered into the offgas line and, once cleaned off the filter, returned into the mixer. The SILICA thus laden is reacted in the reactor in the course of a residence time of 1 hour at a wall temperature of 215° C. in the top region of the reactor and a wall temperature of 330° C. in the bottom region of the reactor while being further fluidized by stirring, and then purified in a dryer at 150° C. in the course of a residence time of 0.5 hours. The analytical data are itemized in Table 1.

EXAMPLE 2

Example 1 is repeated except that a trimethylsiloxy-terminal polydimethylsiloxane having a viscosity at 25° C. of 20 mPas is used instead of a dimethylhydroxysiloxy-terminal polydimethylsiloxane. The analytical data are itemized in Table 1.

EXAMPLE 3

Into the continuous plant of Example 1 are added in the mixer at a temperature of 30° C. under inert gas $N_2$, under mechanical fluidization by stirrer, to a mass flow of 900 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D), 100 g/h of dimethyldichlorosilane in liquid, very finely divided form by jetting through a one-fluid nozzle as aerosol (pressure 10 bar) and 100 g/h of completely ion-free water in liquid, very finely divided form by jetting through a one-fluid nozzle as an aerosol (pressure 10 bar). In addition, a further 100 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D) are metered into the offgas line and, once cleaned off the filter, returned into the mixer. The SILICA thus laden is reacted in the reactor in the course of a residence time of 1 hour at a wall temperature of 200° C. in the top region of the reactor and a wall temperature of 235° C. in the bottom region of the reactor while being further fluidized by stirring, and then purified in a dryer at 150° C. in the course of a residence time of 0.5 hours. The analytical data are itemized in Table 1.

EXAMPLE 4

Not in Accordance with the Present Invention

Into the continuous plant of Example 1 are added in the mixer at a temperature of 30° C. under inert gas $N_2$, under mechanical fluidization by stirrer, to a mass flow of 1000 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D), 180 g/h of a dimethylhydroxysiloxy-terminal polydimethylsiloxane having a viscosity at 25° C. of 20 mPas in liquid, very finely divided form by jetting through a one-fluid nozzle as an aerosol (pressure 10 bar). No further silica is metered into the offgas line and returned into the mixer after cleaning off the filter. The SILICA thus laden is reacted in the reactor in the course of a residence time of 1 hour at a wall temperature of 215° C. in the top region of the reactor and a wall temperature of 330° C. in the bottom region of the reactor while being further fluidized by stirring, and then purified in a dryer at 150° C. in the course of a residence time of 0.5 hours. The analytical data are itemized in Table 1.

EXAMPLE 5

Not in Accordance with the Present Invention

Into the continuous plant are added in the mixer at a temperature of 30° C. under inert gas $N_2$, under mechanical fluidization by stirrer, to a mass flow of 1000 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D), 180 g/h of a dimethylhydroxysiloxy-terminal polydimethylsiloxane having a viscosity at 25° C. of 20 mPas in liquid, very finely divided form by jetting through a one-fluid nozzle as an aerosol (pressure 10 bar). In addition, a further 100 g/h of hydrophilic SILICA, having a moisture content below 1% and an HCl content below 100 ppm and having a specific surface area of 200 $m^2/g$ (measured by the BET method to DIN 66131 and 66132) (obtainable under the name WACKER HDK N20 from Wacker Chemie AG, Munich, D) are metered into the offgas line and, once cleaned off the filter, returned into the reactor. The SILICA thus laden is reacted in the reactor in the course of a residence time of 1 hour at a wall temperature of 215° C. in the top region of the reactor and a wall temperature of 330° C. in the bottom region of the reactor while being further fluidized by stirring, and then purified in a dryer at 150° C. in the course of a residence time of 0.5 hours. The analytical data are itemized in Table 1.

TABLE 1

|  | Loss of organo-Si [%] | Water-wettable fraction [%] | Pressure drop at filter after 2 h [mbar] | Carbon content [%] |
|---|---|---|---|---|
| Ex. 1 | 17.1 | 0 | 1 | 4.1 |
| Ex. 2 | 18.3 | 0 | 1 | 4.5 |
| Ex. 3 | 13.7 | 0.08 | 3 | 1.8 |
| Ex. 4* | 27.2 | 2.7 | 70 | 3.6 |
| Ex. 5* | 19.2 | 0.3 | 10 | 4.0 |

*not in accordance with the present invention

What is claimed is:

1. A process for producing surface modified particulate finely divided solid F having a BET surface area of from 0.1 $m^2/g$ to 1000 $m^2/g$, comprising the steps of:
   (A) mixing a first amount of unmodified finely divided solid F1 with organosilicon compound(s) to form a first mixture of F1 and organosilicon compound(s) and producing an offgas comprising organosilicon compound(s);
   (B) reacting the mixture of unmodified finely divided solid F1 with organosilicon compound(s) to produce surface modified finely divided solid F with or without an offgas comprising organosilicon compound(s);
   (C) freeing the surface modified finely divided solid F from step (B) of adsorbed byproducts and unconverted organosilicon compound(s) which are obtained as offgas;
   (D) metering a second amount of unmodified finely divided solid F1 into the offgas obtained in process steps (A), (C) or (B) putting in upstream of a filter to mix the solid F1 with organosilicon compound(s) in the offgas to form a second mixture of F1 and organosilicon compound(s); and
   (E) feeding the second mixture obtained in process step (D) to process step (A) to augment the first mixture of unmodified finely divided solid F1 and organosilicon compound(s).

2. The process of claim 1, wherein at least one organosilicon compound is an organosilane of formula (I)

$$X_{1+x'}\text{—}SiR^4{}_{2-x'}\text{—}(CH_2)_v\text{—}Y \qquad (I),$$

where
X each independently represents halogen, nitrogen, $OR^3$ or $OCOR^3$,
$R^3$ each independently represents C—O bonded $C_1$-$C_{15}$ hydrocarbyl or acetyl,
$R^4$ each independently represents a hydrogen atom or optionally NC—, OCN—, $2R^2$N—, HOOC—, $R^2$OOC—, halogen-, acryloyl-, epoxy-, HS—, HO— or $2R^2$NOC-substituted Si—C bonded $C_1$-$C_{20}$ hydrocarbyl or $C_1$-$C_{15}$ hydrocarbyloxy, wherein in each of which one or more nonadjacent methylene units are optionally replaced by —O—, —CO—, —COO—, —OCO—, or —OCOO—, —S—, or —$NR^2$— groups and in which one or more mutually nonadjacent methine units are optionally replaced by —N= or —P=groups,
Y each independently represents hydrogen, unsaturated or mono- or polyunsaturated $C_1$-$C_{20}$ hydrocarbyl, —OC(O)C(R)=$CH_2$, -vinyl, -hydroxyl, -halogen, phosphonato, —NCO, —NH—C(O)—$OR^1$, -glycidoxy, —SH, or acid anhydride,
R, $R^1$ each, independently represent $C_1$-$C_{15}$ hydrocarbyl,
v is from 0 to 10, and
x' is 1 or 2.

3. The process of claim 1, wherein at least one organosilicon compound is an organosiloxane comprising of A units of formula (IIa) and one or more B units of formulae (IIb-d)

$$(R^5{}_3SiO_{1/2}) \qquad (IIa),$$

$$(R^5{}_2SiO_{2/2}) \qquad (IIb),$$

$$(R^5SiO_{3/2}) \qquad (IIc),$$

$$(SiO_{4/2}) \qquad (IId),$$

where the organosiloxanes may contain 1 or 2 —X groups attached to silicon atoms, where X each independently is halogen, nitrogen, $OR^3$, or $OCOR^3$ wherein $R^3$ each independently is C—O bonded $C_{1-15}$ hydrocarbyl or acetyl, and organosiloxanes may contain =SiX or =$SiX_2$ groups in a number C, and A, B and C are subject to the following condition:
1≤B≤5000, with the proviso that B≥A+C, where A+C=0 is subject to the condition 10≤B≤100, while the ratio of A to C is freely choosable, and
$R^5$ each independently represents an optionally mono- or polyunsaturated, monovalent, optionally halogenated Si—C bonded hydrocarbyl of 1 to 18 carbon atoms.

4. The process of claim 2, wherein at least one organosilicon compound is an organosiloxane comprising of A units of formula (IIa) and one or more B units of formulae (IIb-d)

$$(R^5{}_3SiO_{1/2}) \qquad (IIa),$$

$$(R^5{}_2SiO_{2/2}) \qquad (IIb),$$

$$(R^5SiO_{3/2}) \qquad (IIc),$$

$$(SiO_{4/2}) \qquad (IId),$$

where the organosiloxanes may contain 1 or 2 —X groups attached to silicon atoms, where X each independently is halogen, nitrogen, $OR^3$, or $OCOR^3$ wherein $R^3$ each independently is C—O bonded $C_{1-15}$ hydrocarbyl or acetyl, and organosiloxanes may contain =SiX or =$SiX_2$ groups in a number C, and A, B and C are subject to the following condition:
1≤B≤5000, with the proviso that B≥A+C, where A+C=0 is subject to the condition 10≤B≤100, while the ratio of A to C is freely choosable, and
$R^5$ each independently represents an optionally mono- or polyunsaturated, monovalent, optionally halogenated Si—C bonded hydrocarbyl of 1 to 18 carbon atoms is also present.

5. The process of claim 1, wherein process step (B) is conducted in an atmosphere containing less than 2.5% by volume of oxygen.

6. The process of claim 1, which is a continuous process.

7. The process of claim 1, wherein the organosilicon compound(s) are admixed in process step (A) as a finely divided aerosol.

8. The process of claim 1, wherein the mixing with the organosilicon compound(s) in process step (A) and the reacting in process step (B) are effected under mechanical or gasborne fluidization.

9. The process of claim 1, wherein from 1 to 50 parts by weight of solid F1 are metered into the offgas in process step (D) per 100 parts by weight of solid F1 used in process step (A).

10. The process of claim 1, wherein the solids F1 are selected from metal oxides, silicates, aluminates, titanates and aluminum sheet-silicates.

11. The process of claim 10, wherein the solids F1 are selected from precipitated silicas and pyrogenically produced silicas.

\* \* \* \* \*